(12) United States Patent
Yvin et al.

(10) Patent No.: US 6,750,208 B1
(45) Date of Patent: Jun. 15, 2004

(54) MEDICINE FOR TREATING APOPTOSIS DYSFUNCTION CONTAINING OLIGOSACCHARIDES

(75) Inventors: Jean-Claude Yvin, Saint-Malo (FR); Florence Cruz, Saint-Malo (FR); Valérie Descamps, Roscoff (FR); Christophe Richard, Plougourvest (FR); Vesna Thibal, Lyons (FR); Patrick Arrigo, Pers-Jussy (FR); Bernard Cloarec, Saint Pol de Leon (FR)

(73) Assignee: Laboratoires Goemar S.A., Saint Malo (FR)

( * ) Notice: Subject to any disclaimer, the term of this patent is extended or adjusted under 35 U.S.C. 154(b) by 0 days.

(21) Appl. No.: 09/601,665

(22) PCT Filed: Feb. 3, 1999

(86) PCT No.: PCT/FR99/00229

§ 371 (c)(1),
(2), (4) Date: Dec. 28, 2000

(87) PCT Pub. No.: WO99/39718

PCT Pub. Date: Aug. 12, 1999

(30) Foreign Application Priority Data

Feb. 3, 1998 (FR) ............................................. 98 01237

(51) Int. Cl.⁷ ............................................. A61K 31/715
(52) U.S. Cl. ..................................................... 514/54
(58) Field of Search ............................................ 514/54

(56) References Cited

U.S. PATENT DOCUMENTS 5,641,643 A * 6/1997 Tanaka et al. ................. 435/23

FOREIGN PATENT DOCUMENTS

| EP | 0 552 373 | 7/1993 |
|----|-----------|--------|
| EP | 0 795 560 | 9/1997 |
| WO | WO95/02684 | 1/1995 |

OTHER PUBLICATIONS

Raff, "Nature", 356, pp 397–400, 1992.
Zablakis E. & Perez J. " *Botanica marina*", 33, pp 273–276, 1990.
Williams et al., "Developement of a water soluble . . . ", Carbohydr. Res., 235, pp 247–257, 1992.
Dulbecco et al., "Virology", 8, pp 396–397, 1959.
Moore et al., "J.A.M.A.", 199, pp 87–92, 1967.
Bing AN et al., "Cell death and differentiation", 5, 1062–1075, 1998.
Hollstein et al., "Nucl. Acid Res." 22, pp 3551–3555, 1994.
Muller et al., J. Exp. Med., 188, pp 2033–2043,1998.
Juo et al., Curr. Biol., 8, pp 1001–1008, 1998.
Abstract of "Biochem Z" 215, pp 30–60, 1929.
Bortner et al., "Trends in cell. Biol", 5, p21, 1995.
Science, "Green", 278, p 1246, 1997.

* cited by examiner

*Primary Examiner*—Raymond J. Henley, III
(74) *Attorney, Agent, or Firm*—Kilpatrick Stockton, LLP

(57) ABSTRACT

The invention concerns a medicine comprising, as active principle, an efficient quantity of at least an oligosaccharide substance capable of modulating apoptosis dysfunction which is capable of modifying apoptosis dysfunctions said substance being selected from the group consisting of oligosaccharides which are derived, by enzymatic or chemical process, from the polymers of the group comprising (1→3)-β-glucans which optionally comprise (1→6)-β-branching, and oligosaccharides which are derived, by enzymatic or chemical process, from sulfated galactans, it also concerns a method for treating apoptosis dysfunction.

18 Claims, 8 Drawing Sheets

MEDICINE FOR TREATING APOPTOSIS DYSFUNCTION CONTAINING OLIGOSACCHARIDES

This is a 371 of PCT/FR99/00229 filed Feb. 3, 1999.

The subject of the invention is a medicine for treating apoptosis dysfunctions.

The term <<apoptosis>> is intended to refer to programmed cell death or cell suicide.

This death corresponds to a self-elimination of cells according to a defined program.

It reveals itself, initially, through bulges in the plasma membrane, these bulges being accompanied by a structural change in the membrane, and then through a loss of volume of the cell, which appears to contract and to collapse in on itself.

The nucleus condenses and the DNA is cleaved into small fragments (Raff, <<Nature>>, 356, 397, 1992; Bortner et al., <<Trends in Cell. Biol.>> 5, 21, 1995).

In vivo, the cell undergoing apoptosis is recognized by macrophages which will phagocytose it and eliminate it without any inflammatory process.

Still in vivo, apoptosis is widely used by living organisms to control cell populations, in particular lymphocytes subsequent to their activation.

Moreover, during the development of organisms, apoptosis plays a fundamental role in the elimination of unnecessary embryonic tissues (lizard tail, rudiment of the genital organs of one sex or the other) and in the pattern of the organism (elimination of the interdigital webs between the future fingers etc.).

Some compounds which are present in living organisms specifically induce an apoptotic phenomenon. Thus, for example in mammals, the binding of the Fas ligand to the Fas membrane-bound receptor, which is also referred to as APO-1 or CD95, specifically induces an apoptosis; this apoptosis is used by the living organism to control lymphocyte populations, in particular T lymphocyte populations.

The abovementioned receptor and ligand represent an extremely advantageous physiological system which is involved in the specific elimination of cells which are no longer desired in the organism.

Mention may be made in particular of cell elimination during the maturation and activation of T lymphocytes. In fact, the Fas system, i.e. Fas ligand/Fas receptor, plays a fundamental role in the homeostasis of the immune system.

The Fas receptor is a member of a family of proteins which act as cell surface receptors and which also comprise the TNF (tumor necrosis factor) and NGF (nerve growth factor) receptors.

The Fas receptor is expressed in many cells; it is thought to accumulate in the Golgi apparatus.

The mechanism by which the Fas system induces cell death in unknown, but involves the activation of the proteases which are known under the designation ICE-like (<<interleukin-1 beta-converting enzyme>>) or caspases.

It may be noted that the Fas ligand can be secreted by cells in order to induce their own suicide; but given that this ligand is also found at the surface of activating cells, these cells will, as a result, induce the suicide of target cells by simple contact. Once it has been activated, the Fas receptor interacts with many intracellular proteins so as to transmit the apoptosis-triggering signal.

In vitro, other means exist for inducing apoptosis, for example by inhibiting the activity of certain kinases, and in particular kinase C; in this case, staurosporin may be used.

This product is very effective for inducing cell death by apoptosis.

It should, however, be noted that the signal transduction which is induced by staurosporin is different from that involving the Fas receptor.

However, while the means of activating apoptosis are different, the execution of the death program which is induced by these two modes of activation is equivalent and is characterized by an activation of the caspase cascade and a dysfunction of mitochondria, which releases compounds (for example, the cytochrome C) which will promote the programmed destruction of the cell. This phenomenon is energy-dependent, but does not require the synthesis of new proteins. In fact, in a cell, everything is ready for it to carry out its own destruction.

In vivo, the regulation of the apoptotic phenomenon has a considerable importance.

Specifically, many pathologies are associated with its dysfunction.

Mention may be made, for example, of two cases of apoptosis dysfunction in which the apoptosis is modified via the Fas system; they are autoimmune diseases in which apoptosis is deficient and the destruction of HIV-1-infected CD41 T lymphocytes in which apoptosis is too active.

In other cases such as the neuronal degeneration which is encountered, for example, in multiple sclerosis, apoptosis is activated via pathways which are as yet unknown.

Other pathologies exist in which apoptosis is deficient; in this respect, mention may be made of the accumulation of cancer cells in which apoptosis would appear to depend on the FAS system (<<Green>>, Science, vol. 278, 1246, 1997).

In light of the findings recalled above, the applicant company, to its credit, found that as a result of the availability of a medicine which is capable of modifying apoptosis dysfunctions both from the point of view of an activation, in the case of the pathologies of the group comprising autoimmune diseases and the pathologies such as cancer, and from the point of view of its inhibition, in the case of the pathologies of the group comprising AIDS, it became possible to combat these diseases.

It also found, to its no less great credit, that some oligosaccharide and monosaccharide substances which optionally comprise, on at least some of their individual units, at least one substituent of the group comprising sulfate, methyl and acetyl groups, were capable of modifying apoptosis dysfunctions.

A subject of the invention is thus a medicine, characterized in that it comprises, as an active principle, an effective amount of at least one oligosaccharide substance which is capable of modifying apoptosis dysfunctions and which optionally comprises, on at least some of its individual units, at least one substituent of the group comprising sulfate, methyl and acetyl groups, said substance being chosen from the group comprising:
 the oligosaccharides which are derived, by enzymatic or chemical process, from the polymers of the group comprising (1→3)-β-glucans which optionally comprise (1→6)-β-branching,
 the oligosaccharides which are derived, by enzymatic or chemical process, from sulfated galactans, in particular carrageenans, agars and porphyrans.

According to one advantageous embodiment, the medicine in accordance with the invention comprises, as an active principle, an effective amount of at least one oligosaccharide which is capable of modifying apoptosis dysfunctions and which satisfies the formula:

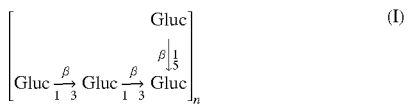

in which n represents an integer from 1 to 50, preferably from 5 to 10, and in which the number of branches varies from 0 to 3 per repeat unit.

According to another advantageous embodiment, the medicine in accordance with the invention comprises, as an active principle, an effective amount of at least one repeat disaccharide which is capable of modifying apoptosis dysfunctions and which satisfies the formula:

in which n represents an integer from 1 to 50, preferably from 1 to 20, at least some of the repeat disaccharides of formula (II) possibly comprising one or more sulfate groups.

According to another advantageous embodiment, the medicine in accordance with the invention comprises, as an active principle, an effective amount of the product which is capable of at least partially inhibiting apoptosis and which is obtained by hydrolysis from sodium iota-carrageenate, this product consisting of a mixture of oligo-iota-carrageenans which is referred to as $I_9$, which has a total saccharide content (determined according to Tillmans and Philippi) of 62%, and which has a distribution profile by size, which is estimated by electrophoresis on polyacrylamide gel according to Zablakis and Perez, of

| | | |
|---|---|---|
| iota-neocarraletraose | (DP 2) | 8–12% |
| iota-neocarrahexaose | (DP 3) | 23–27% |
| iota-neocarraoctaose | (DP 4) | 18–22% |
| iota-neocarradecaose | (DP 5) | 13–17% |
| iota-neocarradodecaose | (DP 6) | 8–12% |
| oligo-iota-carrageenan | (DP 7) | 3–7% |
| oligo-iota-carrageenans consisting of 8 to 15 repeat disaccharides | (DP 8–15) | 13–17%. |

The abovementioned methods are described in <<Botanica marina>>, 33, 273–276 (1990) as regards Zablakis E. & Perez J., and in <<Biochem. Z.>>, 215, 30–60 (1930), as regards Tillmans J. & Philippi K.

In order to prepare the product $I_9$, the following procedure may be carried out.

The iota-carrageenan is incubated in the presence of the partially purified enzyme iota-carrageenase at a temperature of 45 to 50° C., and then the hydrolysis products are ultrafiltered through a 10,000 Da membrane. The product $I_9$ is thus obtained.

More particularly, the iota-carrageenan polymer is hydrolyzed with a recombinant iota-carrageenase which is overexpressed in the strain *Escherichia coli*.

The preparation of the enzyme is carried out by dissolving the bacterial pellet (corresponding to 1 liter of culture) in 50 ml of 10 mM Tris pH 7.5, 100 mM NaCl, 5 mM $CaCl_2$ buffer so as to have a final concentration of 500 U/ml.

From a practical point of view, 100 g of iota-carrageenan substrate are dissolved in 20 l of distilled water while hot (80° C.) so as to obtain at a concentration at 5 g/l, and then the pH is adjusted to 7.5 with ammonium carbonate.

To carry out the hydrolysis, the enzyme is added to 50 U/g of polymer. The continuous ultrafiltration is begun after 30 minutes; it is a tangential ultrafiltration.

For this tangential ultrafiltration, a Pellicon machine comprising a PTGC 0.46 m² 10,000 Da cassette from the company Millipore can be used; this machine is set to 2 bar at inlet and 0.5 bar at outlet.

The filtrate outlet is partially closed in order to maintain the filtration flow rate at 1 liter per hour.

The characteristics of the reaction chamber are chosen so as to allow the enzyme to be supplied with substrate until the 20 l of solution are used up and a fixed volume of 2 liters to be maintained.

18 l are obtained of an ultrafiltrate which is concentrated to 1 liter by rotary evaporation, and then the concentrate is lyophilized. The lyophilisate thus obtained contains the product $I_9$.

The oligocarrageenans of the $I_9$ fraction thus obtained were subjected to an additional fractionation by low pressure chromatography on a P6 Biogel column and then on a Sephadex C10 column.

The fractions identified above are thus obtained.

According to another advantageous embodiment, the medicine in accordance with the invention comprises, as an active principle, an effective amount of the product which is capable of at least partially inhibiting apoptosis and which consists of fraction DP7 of the product $I_9$.

According to another advantageous embodiment, the medicine in accordance with the invention comprises, as an active principle, an effective amount of the product which is capable of activating apoptosis dysfunctions, and which is obtained by acidic aqueous extraction from a brown alga named *Laminaria digitata*, this product consisting of a mixture of oligo-(1→3)-β-glucans which are referred to as $L_{11}$ and comprise from 1 to 50, preferably from 20 to 30, saccharide units, the product in question having the NMR spectrum shown in FIG. 1.

It should be noted that the product $L_{11}$ can also be obtained by aqueous extraction from brown algae in general, of which *Laminaria digitata* is a representative.

The preparation of the product $L_{11}$ can be carried out as follows.

1 l of 0.3% sulfuric acid are gradually added to 300 g of fresh algae such as *Laminaria digitata* which are harvested in the month of August in fresh or dry form.

The procedure is carried out in a water bath at a temperature of approximately 70° C. for 2 hours and 30 minutes with shaking.

This procedure is repeated twice.

The extract obtained is clarified by filtration through a filter with a porosity of 1.2 μm.

The liquid resulting from this filtration is subjected to a tangential ultrafiltration through a membrane with a porosity of 50,000 daltons.

The ultrafiltration is carried out while maintaining a pressure of 1 bar.

An ultrafiltrate whose pH is brought back to 5.5, and which has a volume of approximately 0.8 liters, is thus obtained. This ultrafiltrate is subjected to dialysis on a cellulose ester membrane which has a porosity equal to 500 daltons.

A dialysate is obtained which is concentrated to a volume of 100 ml by evaporating off at 80° C. using a Rotovapor-type machine, and then lyophilized.

7 g of a cream-colored powder which constitutes the product $L_{11}$ are obtained.

Analysis by ionic chromatography coupled with amperometry and using an ion-exchanging resin sold by the company Dionex shows that the oligo-(1→3)-β-glucans which are constituents of the abovementioned powder in fact have 1 to 50, preferably from 20 to 30, saccharide units.

With the chromatographic conditions (so-called HPLC method, i.e. <<High pressure liquid chromatography>>) being as follows:

| | |
|---|---|
| Column | Carbopac PA1 |
| Flow rate | 1 ml/min |
| Detection | amperometric-gold electrode |
| Injection | 50 µl |
| Elution gradient | 50 mM sodium hydroxide/500 mM sodium acelate-demineralized water |
| Analysis time | 15 minutes |
| Retention time | ≈ 9–10 minutes | the curve which is shown in FIG. 16 was obtained which identifies the product $L_{11}$.

The examination of the $^{13}C$ NMR spectrum of the product $L_{11}$, which was carried out using an 80 mg/ml solution in $D_2O$ and which is represented in FIG. 1, shows a (1→3)-β-D-glucan backbone for which the resonances of the various carbons were able to be identified (they are assembled in Table A below) by comparison with the values in the literature [see Williams et al., 1992 <<Development of a water soluble, sulfated (1→3) β D-glucan biological response modifier derived from Saccharomyces cerevisiae>>, Carbohydr. Res. 23b: 247:25].

TABLE I

| Chemical shifts (ppm) of the $^{13}C$ NMR spectrum of the sample $L_{11}$ | | |
|---|---|---|
| (1→3)-β-D-glucan backbone | C1 | 102.76 |
| | C2 | 73.41 |
| | C3 | 84.94 |
| | C4 | 68.45 |
| | C5 | 75.89 |
| | C6 | 61.06 |
| D-mannitol residue | C6 | 63.42 |

The medicines in accordance with the invention which are defined above comprise the adjuvants of conventional formulation corresponding to their mode of administration and dose used.

A subject of the invention is also a method for preparing a medicine for treating apoptosis dysfunctions, characterized in that a pharmaceutical composition comprises at least one of the active principles identified above.

According to one advantageous embodiment, the abovementioned pharmaceutical composition is suitable for intravenous administration.

Figure 1:
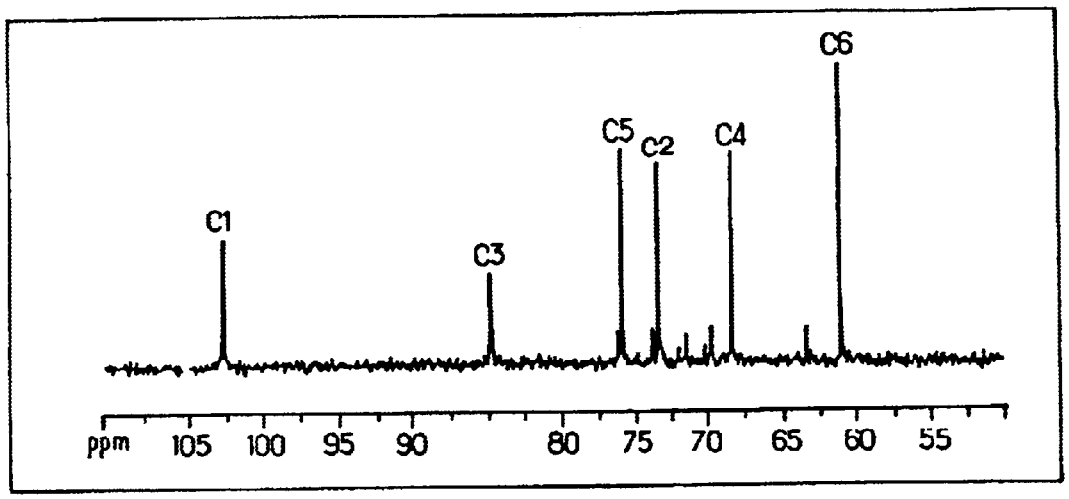
FIG. 1 shows a $^{13}C$-NMR spectrum of the product referred to as $L_{11}$.

The invention is also directed toward the use, with a view to preparing a medicine for treating apoptosis dysfunctions, of the saccharide substances of the group comprising the oligosaccharides which are derived, by enzymatic of chemical process, from the polymers of the group comprising (1→3)-β-glucans which optionally comprise (1→6)-β-branchings, and the oligosaccharides which are derived, by enzymatic or chemical process, from sulfated galactans, in particular carrageenans, agars and porphyrans.

More particularly, it is directed toward the use, with a view to preparing a medicine for treating apoptosis dysfunction, of the oligosaccharides of formula (I) and of those of formula (II).

Even more particularly, it is directed toward the use of the products which are referred to as $I_9$ and $L_{11}$ and of fractions DP 2 and DP 7 of $I_9$ with a view to preparing medicines for treating apoptosis dysfunctions.

The invention will be even better understood with the aid of the further description which follows and of the examples which are in no way limiting, but which correspond to advantageous embodiments.

In the experiments which will be described below, work was carried out on cell cultures in which an apoptotic process was triggered using the Fas system or staurosporin, and then the modification effects possibly obtained with the products which constitute the active principle of the medicines in accordance with the invention were studied.

In the context of these experiments, on the one hand, the suitable amounts of active principle to obtain the desired effect of apoptosis modification and, on the other hand, the moment(s) at which it is suitable to administer the active principle or the medicine comprising it in order to obtain the desired modification effect were determined.

EXAMPLE 1

Work was carried out on a culture of murine fibroblasts which were genetically modified so as to constitutively express the human Fas receptor; the active principle tested was the product which is referred to as $I_9$.

In a prior experiment, it was shown that the murine fibroblasts are destroyed by apoptosis when they are placed in the presence either of the Fas ligand or of an agonist antibody which recognizes the Fas receptor and which, in the text hereinbelow, is referred to as kFasAb.

In another prior experiment, it was determined that the present $I_9$ did not impair cell growth, that it was not toxic with respect to the murine fibroblasts at the concentrations used and that it could thus be added to a cell culture medium without creating problems.

The medium used for culturing the murine fibroblasts is that sold by the company Life Technologies under the name <<Dulbecco's Modified Eagle Medium>>; this medium is described in <<*Virology*>> 8, 396 (1959) by Dulbecco et al.

5% by volume of fetal calf serum was added to this medium.

This medium was then inoculated with murine fibroblasts in the presence of a sufficient amount of antibiotics to eliminate the possibilities of contamination; the fibroblast concentration of the culture medium was $10^5$ cells per ml of medium.

Culturing was carried out in an incubator in which the temperature was kept at 37° C.; the atmosphere filling the incubator contained 5% $CO_2$.

After 24 hours of incubation, either the Fas ligand or the FasAb was directly added to the medium.

The amount of FasAb added was 50 µg per ml of culture medium.

Under these conditions, approximately 70% of the cells of the culture are destroyed by apoptosis after approximately 24 hours of incubation.

This destruction is revealed by crystal violet staining of the surviving cells.

A certain number of assays were then carried out which were intended to demonstrate the action of the active principle.

In these assays, on the one hand, the concentration at which the active principle is used in the culture medium and, on the other hand, the moment at which the active principle is added to this medium were varied so as to determine the optimal active principle concentrations, as well as the most appropriate moment(s) for introducing the active principle with respect to adding the FasAb.

The active principle concentrations were varied from 0.001 to 2 mg per ml.

Successive studies of the effect obtained by first of all adding the active principle before, then at the same time and finally after FasAb were carried out.

In a first assay, the active principle was added 24 hours before FasAb.

In the context of this assay, the effect obtained using successively 0, then 5, then 10, then 50, then 100 and finally 500 ng of FasAb per ml of culture and, in each case, active principle concentrations which were successively equal to 0.25, then 0.5 and finally 1 mg per ml of culture medium was scored, it being understood that the effect obtained in the absence of active principle, i.e. for a concentration of 0%, was also scored.

After 24 hours of incubation, the survival analysis is carried out.

Figure 2:
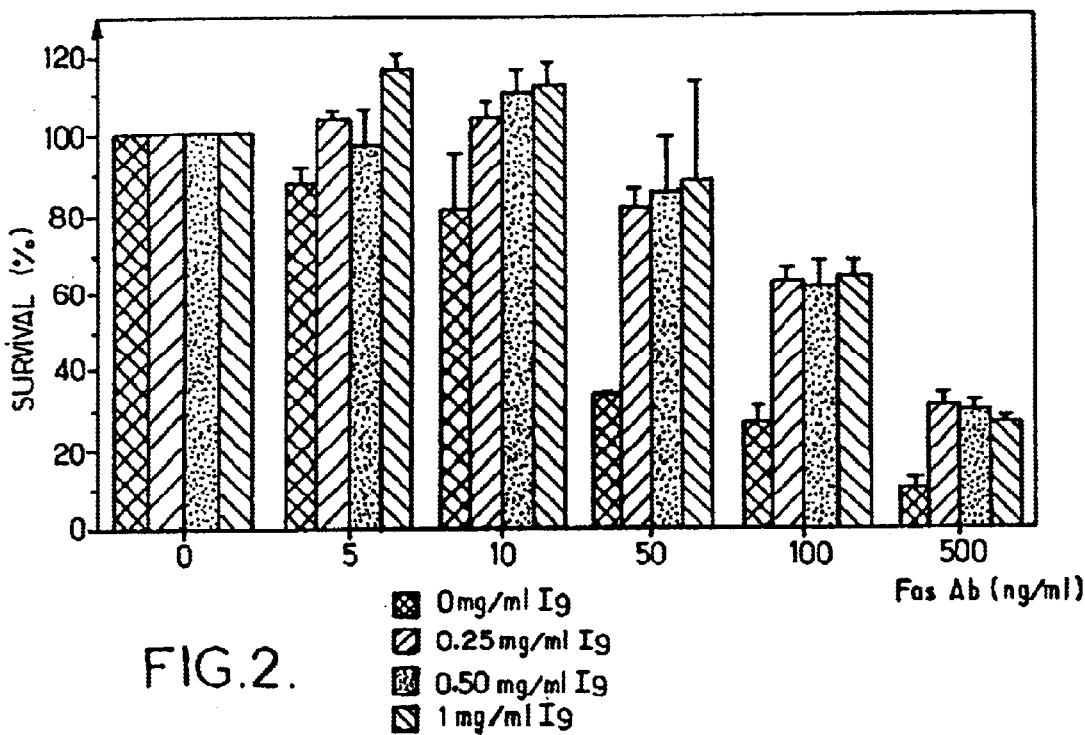
FIG. 2 shows a histogram showing the results of the first test of example 1.

The result of this analysis is indicated by the histogram in FIG. 2.

The FasAb concentration of the medium expressed in ng/ml is shown on the x-axis of this histogram, and the level of survival expressed as % is shown on the y-axis.

For each of the FasAb concentrations, the level of survival for each of the four active principle concentrations, i.e. 0 mg/ml, 0.25 mg/ml, 0.5 mg/ml and 1 mg/ml, has been indicated with four rectangles which are parallel to the y-axis, the standard deviation being indicated each time with a segment which is situated on top of the corresponding rectangle, running parallel to the y-axis.

Each time, the rectangle corresponding to 0 mg/ml of active principle is the one which is located on the far left, the one corresponding to 0.25 mg/ml of active principle is located on its right, the one corresponding to 0.5 mg/ml is located to the right of the previous one, and so on.

Each time, the four rectangles are identified by characteristic hatchings, dots or shadings.

The examination of the results thus collated on the histogram in FIG. 2 shows that, in the absence of active principle, the level of survival decreases as the FasAb concentration increases, and that this level of survival is noticeably improved by adding the active principle.

In a second assay, the FasAb and the active principle were added to the culture medium at the same time.

In this second assay, the effect obtained using successively the same FasAb and active principle concentrations as in the first assay was scored.

After 24 hours of incubation, the survival analysis is carried out.

Figure 3:
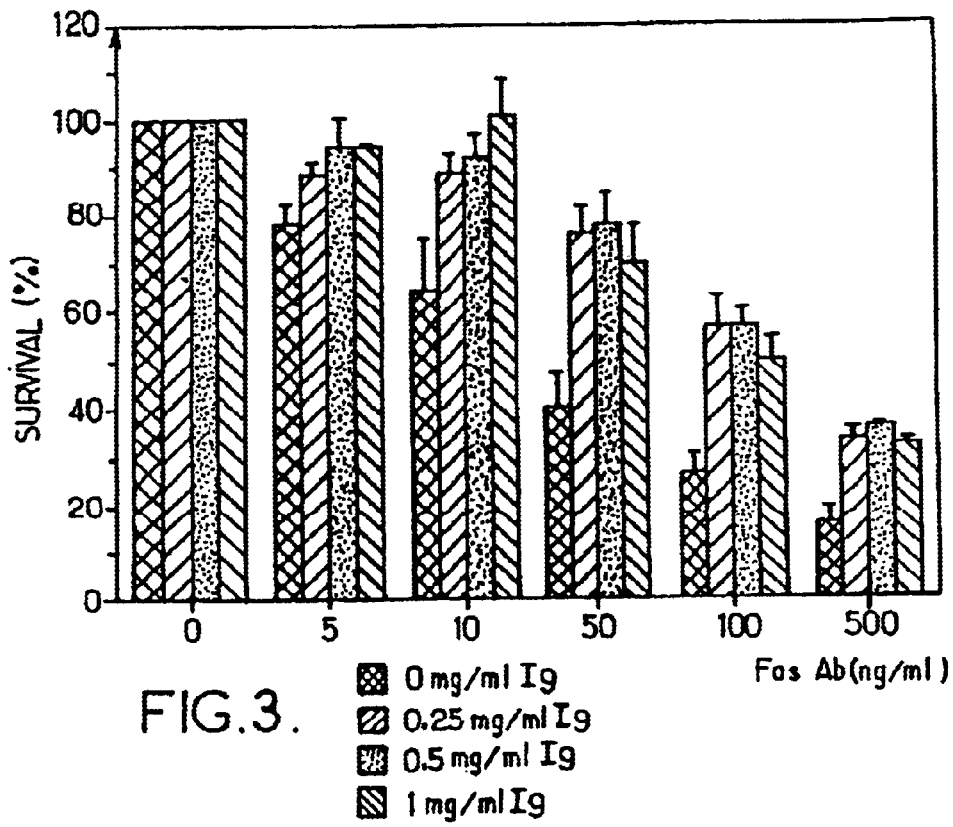
FIG. 3 shows a histogram showing the results of the second test of example 1.

The results recorded are collated on the histogram in FIG. 3, which is prepared according to the same principles as those set out with respect to the one in FIG. 2.

The examination of these results shows that the level of survival evolves in a way which is similar to that scored for the first assay.

In a third series of assays, the active principle was added after FasAb, i.e. successively:
first of all, 1 hour after the FasAb,
then, 3 hours after the FasAb and,
finally, 6 hours after the FasAb.
always varying the FasAb concentration from 0 to 500 ng per ml of culture.

Figure 4:
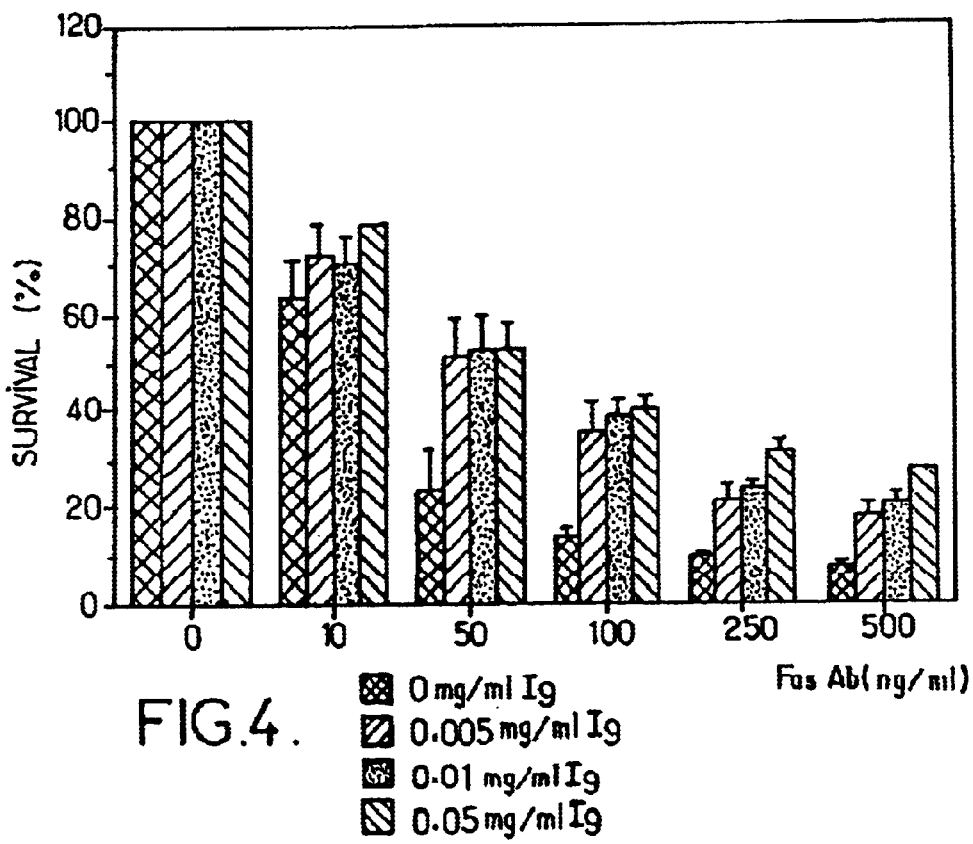
FIG. 4 shows a histogram showing the results of the third test of example 1 with $I_9$ concentrations of 0 mg/ml, 0.005 mg/ml, 0.01 mg/ml and 0.05 mg/ml.
Figure 5:
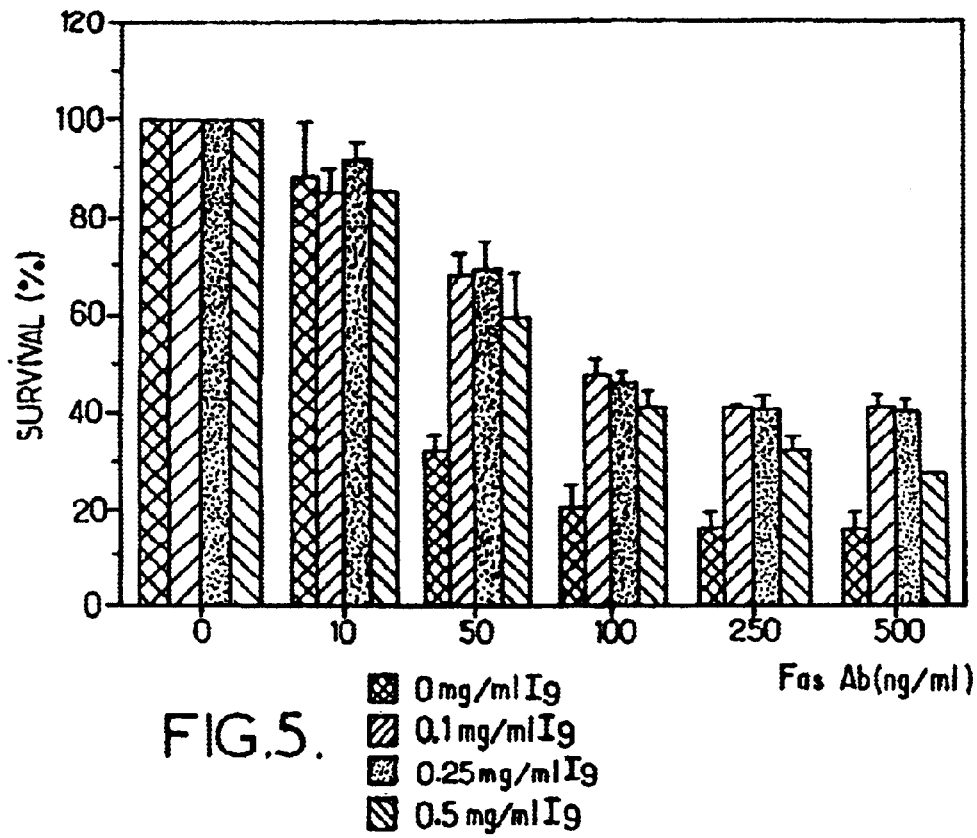
FIG. 5 shows a histogram showing the results of the third test of example 1 with $I_9$ concentrations of 0 mg/ml, 0.1 mg/ml, 0.25 mg/ml and 0.5 mg/ml.
Figure 6:
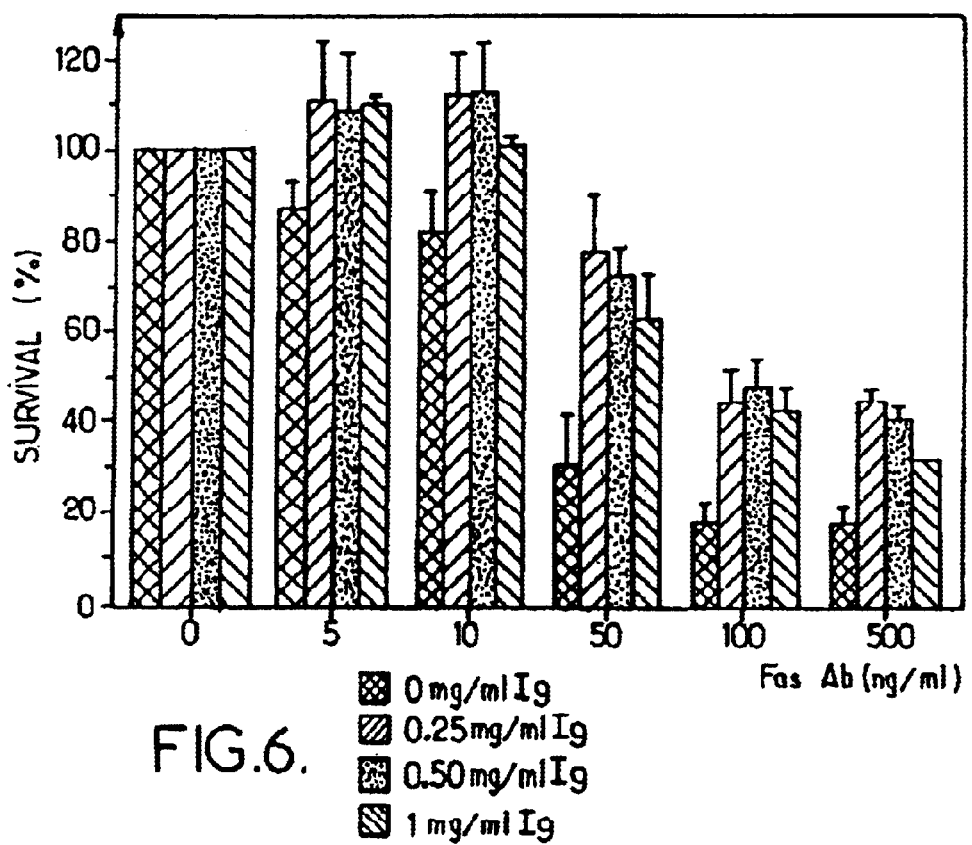
FIG. 6 shows a histogram showing the results of the third test of example 1 with $I_9$ concentrations of 0 mg/ml, 0.25 mg/ml, 0.5 mg/ml and 1 mg/ml.

In the case of the addition of active principle carried out 1 hour after the FasAb,
the results which were scored for $I_9$ concentrations of 0 mg/ml, of 0.005 mg/ml, of 0.01 mg/ml and finally of 0.05 mg/ml have been collated on the histogram in FIG. 4,
the results which were scored for $I_9$ concentrations of 0 mg/ml, of 0.1 mg/ml, of 0.25 mg/ml and finally of 0.5 mg/ml have been collated on the histogram in FIG. 5, and
the results which were scored for $I_9$ concentrations of 0 mg/ml, of 0.25 mg/ml, of 0.5 mg/ml and finally of 1 mg/ml have been collated on the histogram in FIG. 6.

The histograms in FIGS. 4 to 6 are prepared according to the same principles as those set out with respect to the one in FIG. 2.

Figure 7:
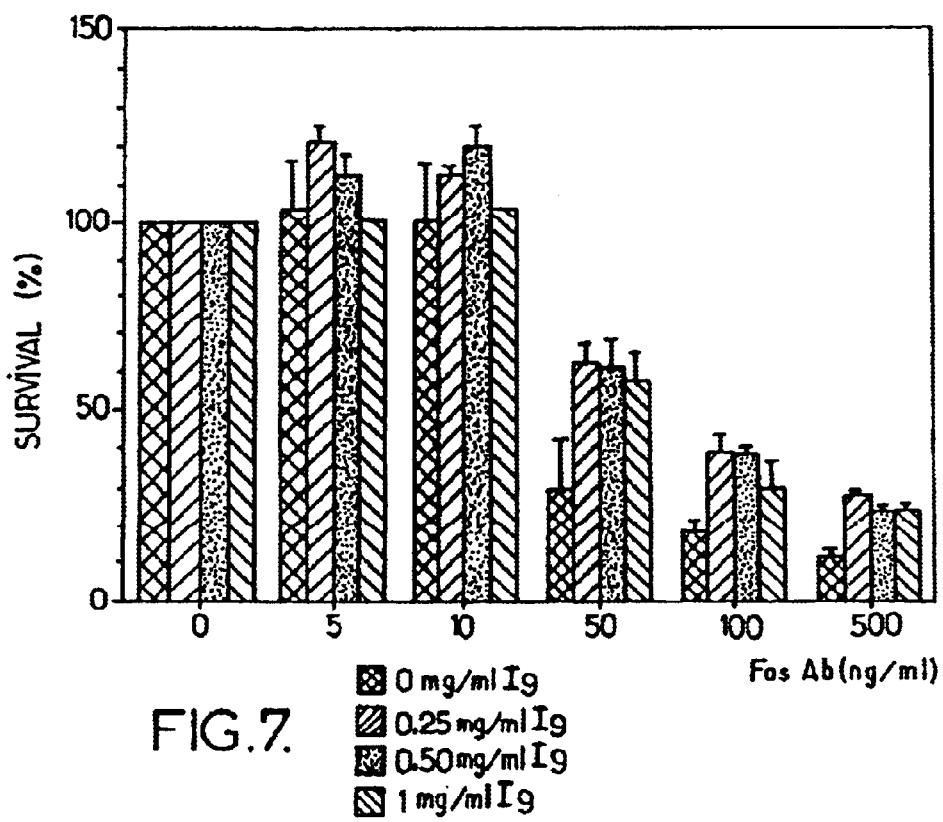
FIG. 7 shows a histogram showing the results of the test of example 1 in which the active principle is added 3 hours after FasAb addition.

In the case of the addition of active principle carried out 3 hours after the addition of FasAb, the results which were scored for $I_9$ concentrations of 0 mg/ml, of 0.25 mg/ml, of 0.5 mg/ml and of 1 mg/ml have been collated on the histogram in FIG. 7.

Figure 8:
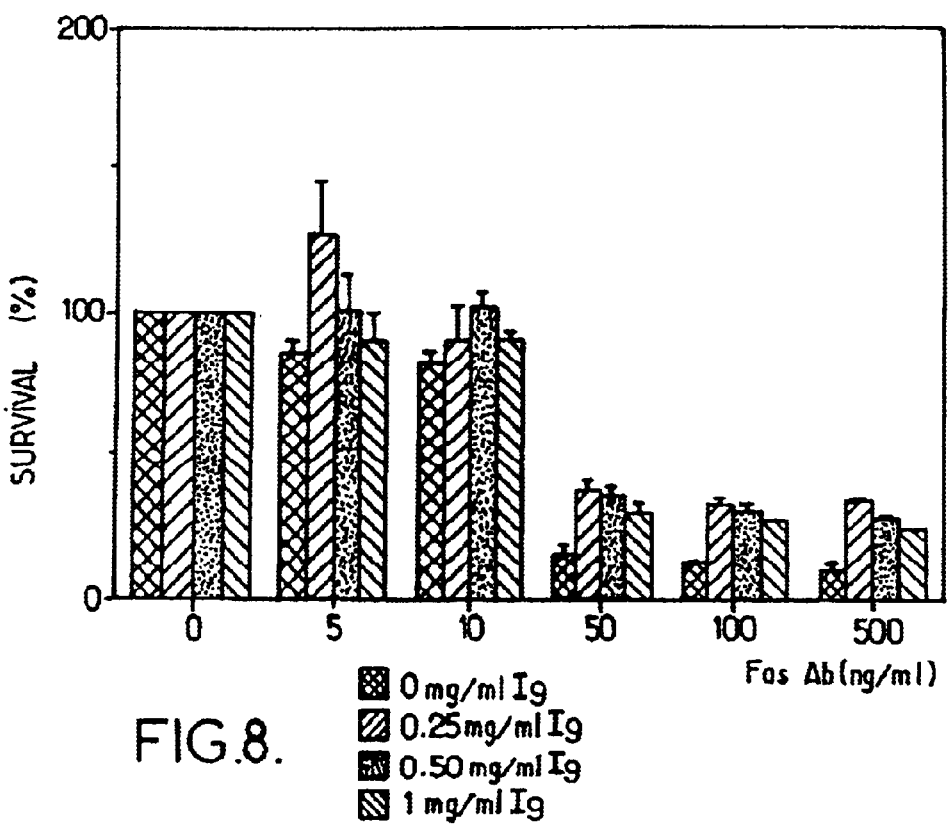
FIG. 8 shows a histogram showing the results of the test of example 1 in which the active principle is added 6 hours after FasAb addition.

In the case of the addition of active principle carried out 6 hours after the addition of FasAb, the results which were scored for $I_9$ concentrations of 0 mg/ml, of 0.25 mg/ml, of 0.5 mg/ml and of 1 mg/ml have been collated on the histogram in FIG. 8.

The histograms in FIGS. 7 and 8 are prepared according to the same principles as those set out with respect to the one in FIG. 2.

The examination of all of the results which are collated on the histograms in FIGS. 4 to 8 shows that, in the case of adding the active principle after adding FasAb, the level of survival always increases; this effect has, however, a tendency to decrease when the time elapsed between the successive additions of FasAb and of active principle increases; moreover, it is sensitive to the active principle concentration when this concentration is lower than 0.25 mg/ml; no noticeable improvement is obtained for concentrations higher than 0.25 mg/ml.

In the experiment which has just been described, apoptosis was induced with the FasAb system.

Another experiment was carried out inducing apoptosis with the kinase inhibitor consisting of staurosporin.

It is recalled that staurosporin induces an apoptotic death in the case of most cells at doses varying from 0.5 to 5 $\mu$M.

In this experiment, the addition of staurosporin and of $I_9$ was simultaneous.

Two doses of $I_9$ were used, i.e. 0.2 mg/ml and 0.5 mg/ml.

Staurosporin was used in a proportion of 0.5 $\mu$M, then of 1 $\mu$M and finally of 1.5 $\mu$M.

The level of survival of the treated cells was determined in each case after 18 hours of incubation.

Figure 9:
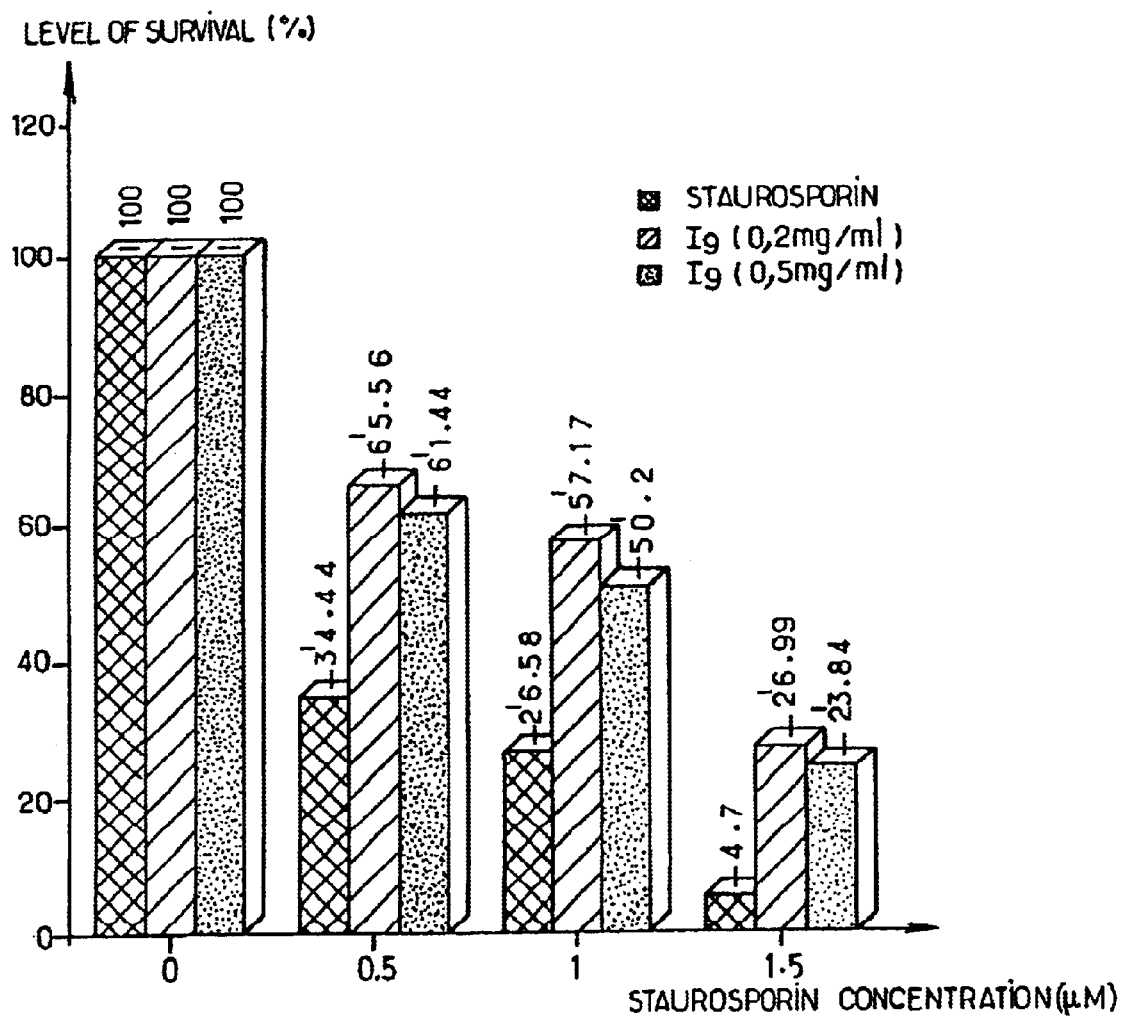
FIG. 9 shows a histogram showing the results of the test of example 1 in which $I_9$ and staurosporin are added simultaneously.

The results recorded appear on the histogram which is represented in FIG. 9 and which shows the level of survival expressed as % as a function of the staurosporin concentration and for the doses of $I_9$ identified above.

A control experiment was carried out for a staurosporin concentration of 0 $\mu$M.

The examination of the results which appear in the histogram shows that the use of $I_9$ attenuates staurosporin-induced apoptosis.

From the two experiments which have just been described, it results that the medicine in accordance with the invention makes it possible to obtain a significant attenuation of apoptosis when this apoptosis is induced with various agents.

EXAMPLE 2

In this example, the cell culture studied was a culture of immortalized human cells consisting of T lymphocytes (Jurkat-type).

The culture medium used is that sold by the company Life Technologies under the name <<RPMI 1640 Medium>>; this medium is described by Moore et al. in the publication <<A.M.A.>> 199, 519 (1967).

10% by volume of fetal calf serum and antibiotics so as to eliminate the possibilities of contamination are added to this medium.

This medium is inoculated with an amount of $10^6$ T lymphocytes per ml of medium.

The temperature of the incubation is −37° C. and the atmosphere filling the incubator contains 5% $CO_2$.

After 24 hours of incubation, the FasAb and the active principle are added simultaneously.

The amount of FasAb (it is the one which is manufactured by he company Upstate Biotechnology and sold under the catalog No. 05-201 by the company Euromedex) added is 50 ng/ml of culture.

The active principle consists successively of the product $I_9$ and the product $L_{11}$.

In each case, the amounts used are 0.5 mg/ml.

The survival analysis is carried out 18 hours after the start of the experiment.

This survival analysis consists in passing a volume of culture containing $10^4$ cells through a machine of the type which functions by flow cytometry, in this case the one sold by the company Beckton Dickinson under the name <<FAC Scan cytometer>>.

This machine uses a probe which detects the presence of phosphatidylserine at the surface of cells; the presence of this product shows that the cells in question are apoptotic.

The results of this analysis appear in FIGS. 10 to 13 in each of which three polygons, A, B and C, respectively, are represented, the contours of which are defined so as to be representative of distinct cell populations; polygon A surrounds a set of living cells, polygon B a set of apoptotic cells and polygon C a set of dead cells.

The percentages of living cells and of apoptotic cells and the percentage of dead cells in the case of each of FIGS. 10 to 13, which will be commented upon below, have been collated in Table II hereafter.

TABLE II

|  | Living cells polygon A | Apoptotic cells polygon B | Dead cells polygon C |
| --- | --- | --- | --- |
| Control (FIG. 10) | 97% | 1% | 1% |
| FasAb (FIG. 11) | 77% | 21% | 1% |
| FasAb/Ia (FIG. 12) | 90% | 2% | 6% |
| FasAb/$L_{11}$ (FIG. 13) | 74% | 13% | 9% |

Figure 10:
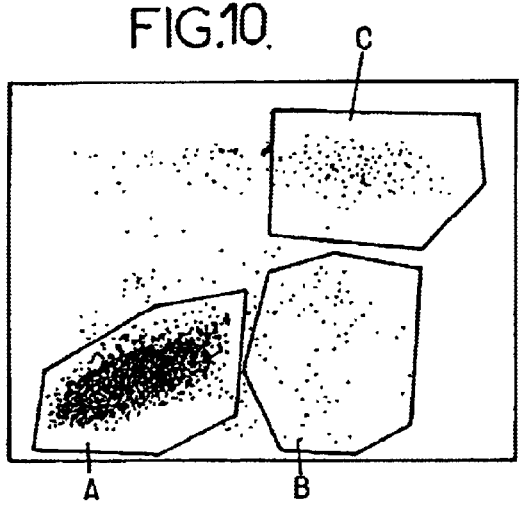
FIGS. 10–13 show a graph illustrating the results of the survival analysis of example 2.

FIG. 10 illustrates the survival analysis carried out on a sample of a culture medium to which neither FasAb nor active principle were added; it is a control; in this case, it is seen that there are essentially only living cells, which are in a polygon A (see line 1 of Table II).

Figure 11:
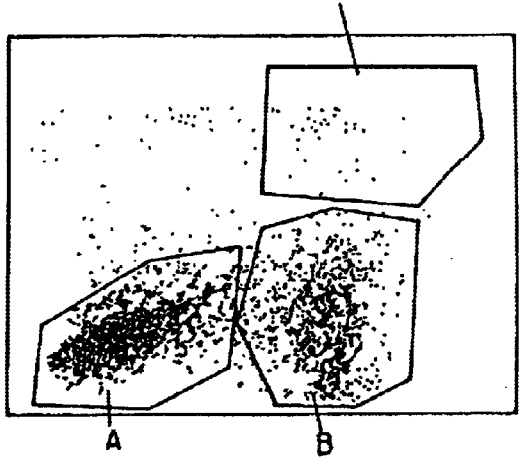

FIG. 11 illustrates the survival analysis carried out on a sample of a culture medium to which only FasAb was added; in this case, it is seen that polygon B contains 21% of apoptotic cells (see line 2 of Table II).

Figure 12:
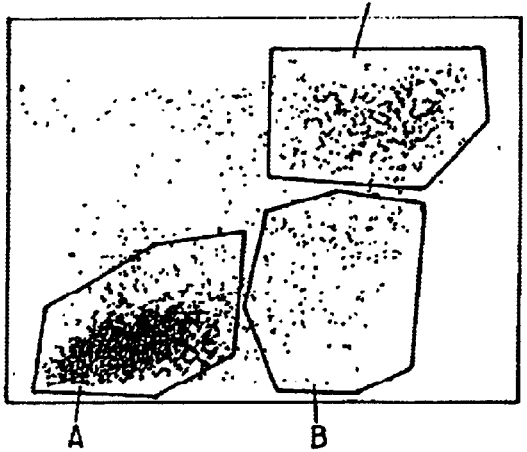

FIG. 12 illustrates the survival analysis carried out on a sample of a culture medium to which FasAb and active principle $I_9$ (0.5 mg/ml) were simultaneously added; in this case, it is seen that polygon B contains practically no apoptotic cells (2%), polygon A containing many living cells and polygon C containing a certain concentration (6%) of dead cells (see line 3 of Table II).

Figure 13:
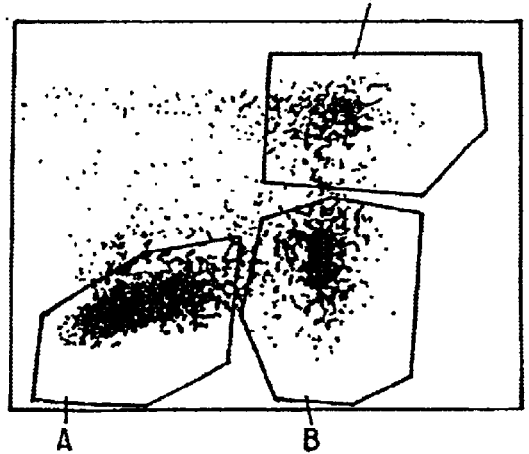

FIG. 13 illustrates the survival analysis carried out on a sample of a culture medium to which FasAb and active principle $L_{11}$ (0.5 mg/ml) were simultaneously added; in this case, it is seen that polygon B contains a considerable amount (13%) of apoptotic cells and polygon C contains a not insignificant amount (9%) of dead cells (see line 4 of Table II).

The conclusions which can be drawn from the examination of FIGS. 10 to 13 and from the analysis of the percentage of the cells present in the various polygons mean, consequently, that the active principle $I_9$, in the context of this experiment, inhibits FasAb apoptosis (the percentage of apoptotic cells goes from 21% to 2%). However, a slight increase in the number of dead cells is noted (this number goes from 1% to 6%). If the number of living cells is considered, a protection of 13% is observed (the percentage goes from 77% to 90%).

With regard to the active principle $L_{11}$, an increase in the number of dead cells (the percentage goes from 1% to 9%) is observed with respect to the effect induced with FasAb only. The principle $L_{11}$, although not inducing a significant effect on the number of living cells, is thus thought to act as a potentiator of cell death.

With the aim of optimizing the $L_{11}$ action, the following experiments were carried out.

Using the same culture as above, there are administered:

in a first experiment, 50 ng/ml of FasAb alone (of Euromedex origin identified above)

in a second experiment, the same amount of the same FasAb simultaneously with 0.5 mg/ml of product $L_{11}$ and in a third experiment, 0.5 mg/ml of the product $L_{11}$ and then, 24 hours later, 50 ng/ml of the same FasAb.

The results obtained after 18 hours of incubation are as follows in comparison with what is observed on a control culture to which neither FasAb nor $L_{11}$ have been added, the value taken into consideration being the number of living cells:

in the case of addition of FasAb alone: the number of living cells decreases by 3.6%, in the case of the simultaneous addition of FasAb and of $L_{11}$, the number of living cells decreases by 6.4% and in the case of the deferred addition of FasAb and of $L_{11}$, the number of living cells decreases by 13.7%.

It ensues that $L_{11}$ is much more active when it is administered before FasAb.

It is indicated that similar results were obtained when replacing the FasAb identified above with a FasAb of another origin, i.e. the one manufactured by the company Alexis Corporation (San Diego, USA) and sold by the company Coger SA (Paris).

It appears, from examining the results of the above experiments, that a medicine based on the product $L_{11}$ makes it possible to potential apoptosis; its use may thus be envisaged in the treatment of diseases of the autoimmune type and of cancer.

Other experiments made it possible to verify the effects produced by the administration of the product $I_9$, on the one hand, in lymphocyte cultures in which a low strength Fas apoptosis was induced and, on the other hand, in the case of lymphocyte cultures in which a high strength Fas apoptosis was induced.

The low strength Fas apoptosis can be induced using a FasAb originating from Euromedex; such an apoptosis can be of the order of 3 to 10%.

The high strength Fas apoptosis can be induced using a FasAb originating from Alexis Corporation; such an apoptosis can be of the order of 20 to 50%.

Figure 14:
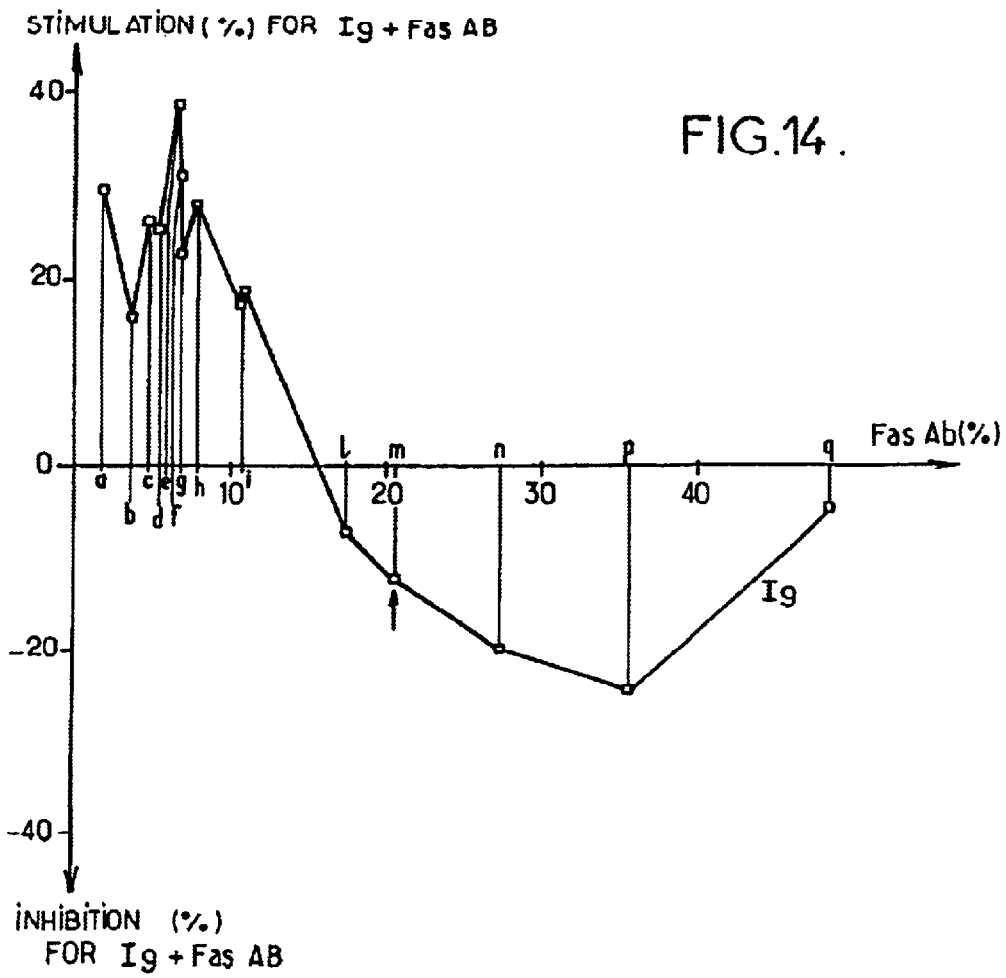
FIG. 14 shows a graph illustrating the stimulation or inhibition of apoptosis caused by 0.2 mg/ml $I_9$.
Figure 16:
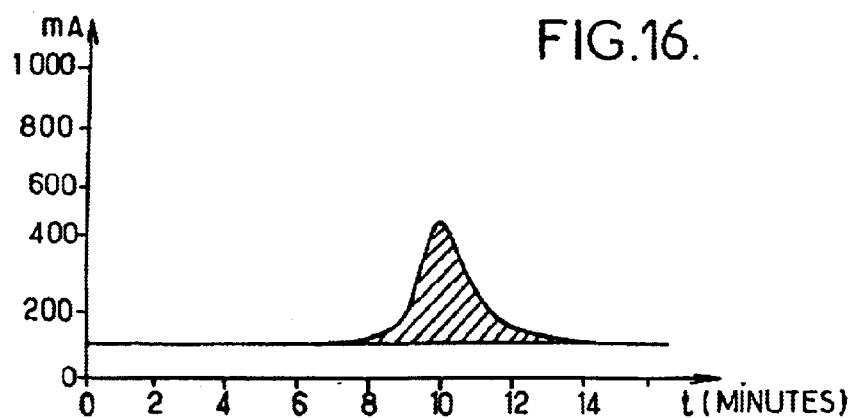
FIG. 16 shows a high pressure liquid chromatography (HPLC) profile of the product referredto as $L_{11}$.

The experiments carried out using a dose of 0.2 mg/ml of the product $I_9$ are illustrated in FIG. 14 which shows the effects recorded, i.e. either the stimulation or the inhibition of apoptosis (expressed as %) as a function of the strength of the apoptosis (as %) induced by FasAb alone (concentrations from 50 to 200 ng/ml).

FIG. 14 shows that in the case of low strength apoptoses, of the order of 3 to 10%, which are indicated on the x-axis by the points a, b, c, d, e, f, g, h and i, the administration of $I_9$ causes a 20 to 40% potentiation of apoptosis with respect to the apoptosis induced by FasAb alone and in the case of high strength apoptoses, of the order of 20 to 50%, which are indicated on the x-axis by the points l, m, n, p and q, the administration of the same amount of $I_9$ causes a 5 to 20% inhibition of apoptosis with respect to the apoptosis produced by FasAb alone.

Knowing that it is possible to determine, in a given individual, the apoptosis induced in lymphocytes, it thus becomes possible to modify it according to the observed strength of said apoptosis in the direction of potentiation or in the direction of inhibition by administering, to this individual, a medicine based on $I_9$.

This medicine may, consequently, make it possible to correct apoptosis in the direction of potentiation when the individual is suffering from a disorder such as cancer or autoimmune disease which corresponds to weak apoptosis, and in the direction of an inhibition when the individual is suffering from a disorder such as immuno-deficiency syndrome which corresponds to strong apoptosis.

This being the case, it is specified that the Jurkat-type T lymphocytes present in the cultures which are subjected to the above experiments are cells in which the tumor suppressor gene p53 or p53 protein (Bing An et al., 1998, <<Cell Death and Differentiation>> 5, 1062–1075) is mutated and, as a result, inactive.

The effects observed with the products used in accordance with the invention, in particular with $I_9$ and $L_{11}$, are thus probably p53-independent; in other words, the products $I_9$ and $L_{11}$ are capable of potentiating the stimulation or inhibition of apoptosis just by virtue of their presence and independently of the presence or absence of the active p53 gene.

Now, in most human cancers (see Hollstein et al., 1994, <<Nucl. Acid Res.>>, 22, 3551), the p53 protein is mutated, and thus inactive; it ensues that the use of a medicine based on one of the products in accordance with the invention, and in particular on the products $I_9$ and $L_{11}$ makes it possible to remedy p53 protein dysfunctions and to treat disorders such as cancer and autoimmune diseases.

The invention makes it possible, consequently, to treat the disorders in question in a way which is fundamentally different and simpler than gene therapy, which is based on the principle aimed in particular at reintroducing a normal p53 gene into the genome of the mutated cells of a sick individual.

It is known that most cancer cells have lost their sensitivity to FasAb apoptosis and that most anticancer agents which are currently used act by activating the p53 gene which, itself, acts positively on the FasAb system. However, these systems no longer function if p53 is mutated (Müller et al. 1998, J. Exp. Med. 188, 2033–2043).

According to recent observations, the FasAb system is capital for the destruction of cancer cells either by the immune system or by the action of anticancer drugs; it ensues that the fact that the products used in accordance with the invention, and in particular $I_9$ and $L_{11}$, modify the apoptosis of said cancer cells in a p53-independent manner is of considerable importance and makes it possible to envisage the development of a novel generation of medicines in particular anticancer medicines.

EXAMPLE 3

The product $I_9$ is composed, as shown above, of a mixture of oligo-iota-carrageenans.

The effect induced by various constituents of this mixture, in particular of fractions DP 2, DP 3, DP 4, DP 5 and DP 7, was tested.

The polymer constituting the raw material of $I_9$ was also tested, as was the product named KIK (hexasaccharide of type kappa-iota-kappa).

For these experiments, the procedure was carried out as in Example 1, simultaneously introducing, on the one hand, 0.2 mg/ml of each of the abovementioned fractions of $I_9$ and, on the other hand, 100 ng/ml of FasAb of Euromedex origin.

After 24 hours of incubation, the findings summarized below were made.

Fractions DP 2, DP 3, DP 4 and DP 5 are inactive and do not stimulate apoptosis induced by a low dose (100 ng/ml)

of FasAb originating from Euromedex which induces, by itself, 6% of cell death after 18 hours of incubation.

Conversely, a very strong stimulatory effect is obtained for fraction DP 7 (50%) and with the product $I_9$ (70%), which shows that one of the active components of the $I_9$ mixture may consist of fraction DP 7; moreover, the product KIK has no activity.

Finally, it was found that the polymer constituting the raw material for the preparation of $I_9$ before cleavage with the enzyme iotase is, it too, active, and stimulates low strength Fas apoptosis. On the other hand, the enzyme iotase itself, used at 50 units, has no activity when it is incubated with the cells.

It ensues that the active principle $I_9$, which has no intrinsic apoptotic activity, induces a very strong stimulation in the case of low strength FasAb apoptosis.

EXAMPLE 4

A further experiment was carried out which confirms the results which are reflected by FIG. 14.

In the case of the apoptotic phenomena induced by Fas, the first of the activated caspase cascade caspases is caspase 8.

Measurement was carried out of the activity of this capsase 8, which is a proteolytic enzyme, after lysis of Jurkat cells which had been treated or not with FasAb alone and with FasAb at the same time as with $I_9$.

To do this, measurement was carried out of
the caspase 8 activity in a first fraction of a culture of Jurkat cells in the absence of FasAb and of $I_9$; the percentage of living cells in the culture is 93%;
the caspase 8 activity in a second fraction of the same culture, 18 hours after incubation with 500 ng/ml of FasAb originating from Euromedex (which, as indicated above, induces weak apoptosis, of the order of 13%); the percentage of living cells in the culture is 80%;
the caspase 8 activity in a third fraction of the same culture, 18 hours after incubation with 500 ng/ml of FasAb originating from Euromedex and of 0.2 mg/ml of $I_9$; the percentage of living cells in the culture is 50%;
the caspase 8 activity in a fourth fraction of the same culture, 18 hours after incubation with 25 ng/ml of FasAb originating from Alexis (which, as indicated above, induces strong apoptosis, of the order of 40%); the percentage of living cells in the culture is 53%;
the caspase 8 activity in a fifth fraction of the same culture, 18 hours after incubation with 25 ng/ml of FasAb originating from Alexis and of 0.2 mg/ml of $I_9$; the percentage of living cells in the culture is 59%;

The measurement of caspase activity was carried out each time using the kit sold by the company Ozyme under the name <<Apo Alert Flice Fluor>> No. K2028-2.

Figure 15:
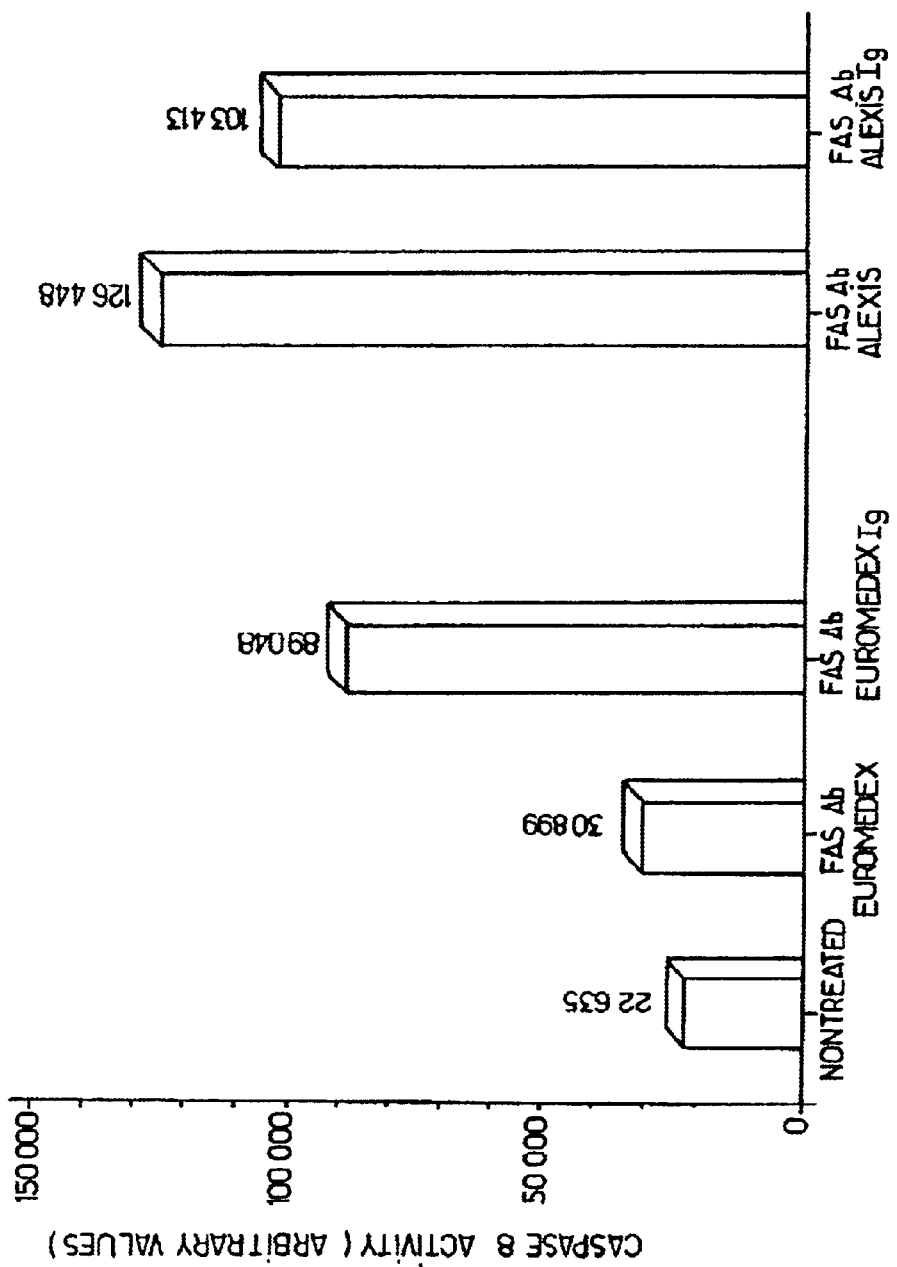
FIG. 15 shows a histogram showing the results of the test of example 4.

The results of these measurements are collated in the histogram in FIG. 15.

The examination of this histogram shows that
the caspase 8 activity is weakly stimulated (factor in the vicinity of 1.37) by Euromedex FasAb alone, the simultaneous administration of $I_9$ inducing a strong stimulation (factor in the vicinity of 3.93);
the caspase 8 activity is strongly stimulated (factor in the vicinity of 4.96) by Alexis FasAb alone, this strong stimulation being decreased (factor in the vicinity of 4.05) when $I_9$ is introduced simultaneously with Alexis FasAb.

Consequently, a clear correlation exists between apoptosis and caspase 8 activity.

The product $I_9$ thus represents a product which is capable of modifying caspase 8 activity.

The fact that it is shown that this enzyme is essential in the biochemical pathway of apoptosis induced by Fas (Juo et al., Curr. Biol. 8, 1001–1008, 1998), makes it possible to envisage novel medicines based on oligosaccharides for targeting enzymes such as caspase.

These products thus represent an alternative to a therapy based on peptides which bear the sequence recognized by caspase 8 (caspase 8 <<suicide substrates>>).

What is claimed is:

1. A medicine comprising as an active principle an effective amount of at least one oligosaccharide substance which is capable of modifying apoptosis dysfunctions, the oligosaccharide substance being selected from the group consisting of oligosaccharides derived by enzymatic or chemical process from sulfated galactans.

2. The medicine according to claim 1, wherein the oligosaccharide substance comprises on at least some of its individual units, at least one substituent of the group consisting of sulfate, methyl and acetyl groups.

3. The medicine according to claim 1, wherein the oligosaccharides are derived from carrageenans, agars or porphyrans.

4. A medicine comprising as an active principle an effective amount of at least one oligosaccharide capable of modifying apoptosis dysfunctions and which satisfies the formula:

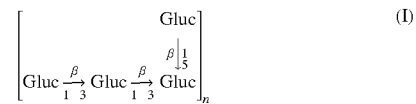

in which n represents an integer from 1 to 50, and in which the number of branches is from 0 to 3 per repeat unit.

5. The medicine according to claim 4, wherein n in formula (I) represents an integer from 5 to 10.

6. A medicine comprising as an active principle an effective amount of at least one repeat disaccharide which is capable of modifying apoptosis dysfunctions and which satisfies the formula:

in which n represents an integer from 1 to 50.

7. The medicine according to claim 6, wherein n in formula (II) represents an integer from 1 to 20.

8. The medicine according to claim 6, wherein at least some of the repeat disaccharides of formula (II) comprises one or more sulfate groups.

9. A medicine comprising as an active principle an effective amount of a product which is capable of partially inhibiting apoptosis and which is obtained by hydrolysis from sodium iota-carrageenate, the product consisting of a mixture of oligo-iota-carrageenans named $I_9$, which has a total saccharide content of 62% and which has a distribution profile by size estimated by electrophoresis on polyacrylamide gel of:

| | | |
|---|---|---|
| iota-neocarratetraose | (DP 2) | 8–12% |
| iota-neocarrahexaose | (DP 3) | 23–27% |
| iota-neocarraoctaose | (DP 4) | 18–22% |
| iota-neocarradecaose | (DP 5) | 13–17% |
| iota-neocarradodecaose | (DP 6) | 8–12% |
| oligo-iota-carrageenan | (DP 7) | 3–7% |
| oligo-iota-carrageenans consisting of 8 to 15 repeat disaccharides | (DP 8–15) | 13–17%. |

10. A medicine comprising as an active principle an effective amount of a product capable of activating apoptosis dysfunction which is obtained by acidic aqueous extraction from brown algae, the product comprising a mixture of oligo-(1→3)-β-glucans named $L_{11}$ and comprising from 1 to 50 saccharide units, the product having the NMR spectrum shown in FIG. 1.

11. The medicine according to claim 10, wherein the brown algae is named *Laminaria digitata*.

12. The medicine according to claim 10, wherein the mixture of oligo-(1→3) β glucans comprises from 20 to 30 saccharide units.

13. A medicine comprising as an active principle an effective amount of a product capable of activating apoptosis dysfunctions and consisting of fraction DP7 of a product named $I_9$.

14. A method for treating apoptosis dysfunctions comprising administering to a patient at least one oligosaccharide substance selected from the group consisting of:

oligosaccharides which are derived, by enzymatic or chemical process, from polymers comprising (1→3)-β-glucans which optionally comprise (1→6)-β-branching, and oligosaccharides which are derived, by enzymatic or chemical process, from sulfated galactans.

15. The method according to claim 14, wherein the oligosaccharide substances comprise on at least some of their individual units, at least one substituent of the group consisting of sulfate, methyl and acetyl groups.

16. The method according to claim 14 wherein the sulphated galactans are carrageenans, agars or porphyrans.

17. A method for treating apoptosis comprising administering to a patient a product selected from the group consisting of oligosaccharides of formula (I) and oligosaccharides of formula (II).

18. A method for treating apoptosis comprising administering to a patient a product selected from the group consisting of products referred to as $I_9$ and $L_{11}$ and a product constituting fraction DP 7 of product $I_9$.

* * * * *